United States Patent [19]

Chastain et al.

[11] Patent Number: 5,308,873
[45] Date of Patent: May 3, 1994

[54] METHOD OF KILLING YEAST AND FUNGI WITH CARVEOL

[75] Inventors: Doyle E. Chastain, 137 Birch St., Titusville, Fla. 32780; W. Eugene Sanders; Christine C. Sanders, both of Omaha, Nebr.

[73] Assignee: Doyle E. Chastain, Titusville, Fla.

[21] Appl. No.: 993,018

[22] Filed: Dec. 18, 1992

[51] Int. Cl.⁵ .................. A01N 31/00; A61K 31/045
[52] U.S. Cl. .................................................. 514/729
[58] Field of Search .................................... 514/729

[56] References Cited

U.S. PATENT DOCUMENTS

| | | | |
|---|---|---|---|
| Re. 28,263 | 12/1974 | Gauvreau | 514/358 |
| 2,803,647 | 8/1957 | Bain et al. | 260/489 |
| 2,863,882 | 12/1958 | Bain et al. | 260/348.5 |
| 3,014,047 | 12/1961 | Bain et al. | 260/348 |
| 3,743,747 | 7/1973 | Whitehurst | 424/333 |
| 5,153,229 | 10/1992 | Chastain et al. | 514/763 |

OTHER PUBLICATIONS

Jour. Amer. Pharm. Assn., Maruzzella et al. vol. 47, No. 4, pp. 250–254 (Apr., 1958).
Plant Disease Reporter, Maruzzella et al. vol. 43, No. 11, pp. 1143–1147 (1959).
Food Technology, Murdock et al. vol. 14, No. 9, pp. 441–445 (1960).
Plant Disease Reporter, Maruzzella et al. vol. 44, No. 10, pp. 789–792 (1960).
Botanical Gazette, French pp. 194–198 (Mar., 1961).
Chemical Abstracts, Blumann et al. vol. 63, p. 1819 (1965).
Nature, Zuckerman vol. 168, p. 517 (Sep., 1951).
Agric. Biol. Chem., Kurita et al. vol. 45, No. 4, pp. 945–952 (1981).
Herba Hungarica, Hethelyi et al. vol. 27, No. 2–3, pp. 89–105 (1988).
Tetenyi et al, C.A. vol. 110 (1989) 110:141367b.

*Primary Examiner*—Allen J. Robinson
*Attorney, Agent, or Firm*—Arthur G. Yeager; Earl L. Tyner

[57] ABSTRACT

A method of killing yeast and fungi which comprises treating the yeast and fungi with a toxic amount of carveol.

3 Claims, No Drawings

METHOD OF KILLING YEAST AND FUNGI WITH CARVEOL

TECHNICAL FIELD

The object of this invention is to demonstrate a method of using carveol to kill yeast and fungi.

BACKGROUND OF THE INVENTION

(1) Field of the Invention

During the study of limonene as a hand cleaner, the applicants found that fully oxygenated limonene is a fungicide. A review of the literature revealed that oxygenated limonene contains several oxidation products including: limonene-1,2-oxide limonene-8,9-oxide, 1-menthene-9-al, α-2,8-p-menthadiene-1-ol β-2,8-p-menthadiene-1-ol, dihydrocarvone, α-cymenol, carvone, cis-carveol and trans-carveol, as was outlined by Bain in U.S. Pat. Nos. 2,863,882 and 3,014,047. Blumann listed the compounds formed by the auto-oxidation of limonene in *Chemical Abstracts*. Volume 63, 1965, on page 1819, which included cis and trans-carveol, trans-p-menth-8-ene-1,2-diol, limonene 1,2-epoxide, limonene 8,9-epoxide, cis and trans-p-mentha-2,8-dien-1-ol, and perillyl alcohol. The applicants found that carveol is a principal anti-yeast and anti-fungal compound generated by the oxidation of limonene and that in effective concentrations carveol kills yeast and in fungicidal concentrations carveol kills fungi.

Carveol is a monocyclic monoterpene with the following chemical formula:

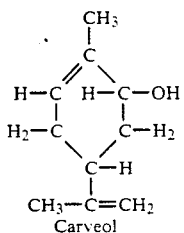
Carveol

Carveol is an oil with a terpenic aroma. It is insoluble in water and glycerine. Carveol is soluble in alcohol and is miscible in corn oil, olive oil, and soybean oil. Carveol has been used as a bactericide but heretofore, it has never been shown to kill yeast or fungi.

Carveol can be produced by the oxidation of limonene as was outlined by Bain in U.S Pat. Nos. 2,863,882 and 3,014,047. Carveol can be obtained from α-pinene, and β-pinene by the Cu+ catalyzed oxidation with benzoyl peroxide as was demonstrated by Walling et. al. in Canadian Patent 981,695. Mestroni et al showed that carveol can be produced by the catalyzed conversion of carvone and dihydrocarvone to carveol as was outlined in German Offen 3,008,671 in the *Chemical Abstracts*, Volume 93, 1980, page 807. Bain, in U.S. Pat. No. 2,803,647 showed his method of producing carveol and dihydrocarveol and their esters. In the Indian Journal of Chemistry, 1975, 13(11), pages 1239–40, Mistra outlined a method of producing carveol and dihydrocarveol from piperitone.

(2) Description of the Prior Art

Zukerman studied the effect of auto-oxidized limonene on bacteria, but found it was weakly bacteriostatic, was unstable, and lost its bacteriostatic effect on keeping as was discussed in *Nature* 168: 517 (1951). He never studied carveol nor the fungicidal activity of auto-oxidized limonene. Kurita investigated the fungicidal activity of several components of essential oils in *Biol. Chem.*, 45(4), 945–952, 1981, and found that cineole, anethole, safrole, d-limonene, α-pinene, β-pinene, camphene, β-myrcene, caryophyllene, β-cymene, δ-camphor, benzaldehyde, vanillin, and furfural are NOT FUNGICIDAL while cinnamaldehyde, phenol, perillyl aldehyde, citral, perillyl alcohol, geraniol, citronellol, 1-nonanol, 1-deconal, 1-menthol and borneol have minimal to good fungicidal activity depending on the component tested. He never studied the anti-yeast nor the anti-fungal activity of carveol. Peter Tetenyi et al studied the essential oils obtained from twelve different specimens of *Tanacetum vulgare L.* and found eight of the twelve oil specimens to be bactericidal in a concentration of 100 ug/ml against 85–90% of nineteen different bacteria and 100% fungicidal against sixteen species of fungi in a concentration of 50 ug/ml. He delineated numerous chemical components in the oils, but he never studied any of those individual components to determine which, if any, had anti-bacterial, anti-yeast, and/or anti-fungal activity as was outlined in *Herba Hungarica*, 1981, Tom 20, No. 1-2, pages 57–74. In the *Botanical Gazette* 122, 194–8 (1961), R. C. French showed that carveol stimulates (rather than inhibits) the germination of wheat stem rust uredospores suggesting that carveol promotes the growth of fungi. Knoblock found that the antimicrobial action of essential oils is related to their ability to penetrate the cell membrane of bacteria and fungi as was shown in the *Journal of Essential Oil Res.* 1989, 1(3), 119–28, but he never demonstrated which components of the es oils, if any, have anti-bacteria, anti-yeast and/or anti-fungal activity. Chastain and Sanders developed a method of making limonene bactericidal and fungicidal as was outlined in U.S. Pat. No.5,153,229, but they never studied carveol for fungicidal activity. Gauvreau showed a means of producing disinfecting compositions in U.S. Pat. No. 3,595,975 by combining cetyl pyridinium with terpenes to form antiseptics. Gauvreau never studied the use of carveol alone nor in combination with cetyl pyridinium. A. Morel revealed the sterilizing action of carveol, dihydrocarveol, and their ozonization products in *Comp. Rend. Soc. Biol.* Volume 115, pages 536–8 (1934). He demonstrated the bactericidal activity of carveol and dihydrocarveol, but he never studied them for anti-yeast or anti-fungal activity. J. C. Maruzzella and L. Liguori reported the in vitro anti-fungal activity of essential oils in the *Journal of the American Pharmaceutical Association*, Vol. XLVII, No. 4, April 1958, pages 250–4, but they did not study the anti-yeast or the anti-fungal activity of carveol. J. C. Maruzzella and Jerry Balter showed the action of essential oils on phytopathogenic fungi in the *Plant Disease Reporter* Vol. 43, No. 11, Nov. 1959, pages 1143–1147, but they did not study the anti-yeast or the anti-fungal activity of carveol. D. D. Whitehead in U.S. Pat. No. 3,743,747 showed the fungicidal activity of several oxo-derivatives of limonene and dipentene, but he never studied the fungicidal activity of carveol. J. C. Maruzzella et al reported the action of odoriferous organic chemicals and essential oils on wood-destroying fungi in the *Plant Disease Reporter*, Vol 44, No. 10 (1960): carveol was not studied. Murdook and Allen showed the germicidal effect of sodium benzoate against yeast is enhanced by orange peel oil and d-limonene (stripper oil), as was reported in *Food Technology*, Vol 14, No. 9, 1960, pages 441–5. They never studied the action of carveol against yeast or fungi. Kellner et al studied ethereal oils for antimicrobial activity, but they never studied the oils nor any of their chemical constituents for anti-yeast or anti-fungal activity as was outlined in Arzneimittel-Forschung 5, 224–9 (1955).

It should be pointed out that the drugs which are bactericidal are usually not fungicidal, and drugs which are fungicidal are usually not bactericidal. In humans, the use of bactericidal antibiotics frequently promotes the growth of yeast. Table A, which follows, exemplifies the anti-bacterial, anti-yeast and anti-fungal activity of several commonly used anti-bacterial, anti-yeast, and anti-fungal antibiotics.

TABLE A

| ANTIBIOTICS | ANTIBIOTIC ACTIVITY AGAINST | | | | |
| --- | --- | --- | --- | --- | --- |
| | Gm + Bact | Gm − Bact | A F Bact | Yeast | Fungi |
| A. ANTIBACTERIAL | | | | | |
| 1. Ampicillin | YES | YES | NO | NO | NO |
| 2. Cephalothin | YES | YES | NO | NO | NO |
| 3. Chloramphenicol | YES | YES | NO | NO | NO |
| 4. Erythromycin | YES | NO | NO | NO | NO |
| 5. Ethambutol | NO | NO | YES | NO | NO |
| 6. Gentamicin | YES | YES | NO | NO | NO |
| 7. Isoniazid | NO | NO | YES | NO | NO |
| 8. Nitrofurantoin | NO | YES | NO | NO | NO |
| 9. Penicillin | YES | NO | NO | NO | NO |
| 10. Rifampin | YES | NO | YES | NO | NO |
| 11. Streptomycin | YES | YES | YES | NO | NO |
| 12. Sulfonamides | NO | YES | NO | NO | NO |
| 13. Tetracycline | YES | YES | NO | NO | NO |
| 14. Vancomycin | YES | YES | NO | NO | NO |
| B. ANTIYEAST | | | | | |
| 1. Nystatin | NO | NO | NO | YES | NO |
| 2. Gentian Violet | NO | NO | NO | YES | NO |
| C. ANTIFUNGAL | | | | | |
| 1. Chlotrimazole | NO | NO | NO | YES | YES |
| 2. Griseofulvin | NO | NO | NO | NO | YES |

Gm+Bact=Gram Positive Bacteria, Gm−Bact=Gram Negative Bacteria, A F Bact=Acid Fast Bacteria, YES=Kills Organism, NO=No Activity Against Organism It should be noted in the table above that none of the anti-bacterial antibiotics kill yeast nor fungi, and none of the anti-yeast nor anti-fungal antibiotics kill bacteria. Thus an anti-fungal or anti-yeast antibiotic is not expected to kill bacteria, and an anti-bacterial antibiotic is not expected to kill yeast nor fungi. Anti-fungal antibiotics do not necessarily kill yeast, and anti-yeast antibiotics do not necessarily kill fungi.

Several significant differences between yeast and fungi are known and are listed. For instance: (1) a yeast culture can be grown in 24–48 hours while a fungus culture requires 7–14 days to grow. (2) Yeast readily grow on blood agar while fungi grow on sabouraud dextrose agar. (3) The use of anti-bacterial antibiotics in humans promotes the growth of yeast but not fungi. (4) Several anti-yeast antibiotics do not kill fungi and several anti-fungal antibiotics do not kill yeast.

DISCLOSURE OF THE INVENTION

This invention relates to the use of carveol to kill yeast and fungi. Carveol is an oil that is available commercially. It is recognized as an anti-bacterial agent, but heretofore, it has not been recognized to have anti-yeast or anti-fungal activity. It is slightly viscous, and when applied, readily adheres to glass, metal, wood, cloth, rope, book covers, paper, cement, ceramics, paint, plastic, plant surfaces, skin, mucus membranes, and teeth leaving an oily film. Because it is not soluble in water its adherence to surfaces allows prolonged exposure and makes carveol ideal for treating yeast or fungus infections of plants, animals, and humans.

The exact method of killing yeast and fungi is unknown, but it is thought that carveol kills yeast and fungi by lysing the cell membrane of the organism which is lethal to the organism.

In practice, any surface on which it is desirable to kill or prevent the growth of yeast or fungi, is treated with effective concentrations of carveol to kill yeast, or fungicidal concentrations of carveol to kill fungi by swabbing, wiping, painting, washing, brushing, spraying, or any other direct application technique. Alternatively, carveol can be incorporated in creams, ointments, tinctures, gels, suppositories, paints, sprays, aerosols, tampons, toothpastes, solutions, emulsions, soaps, scrubs, mouthwashes, or antiseptics and applied anywhere it is desirable to kill or prevent the growth of yeast or fungi.

BEST MODE FOR CARRYING OUT THE INVENTION

The following examples are illustrative of the best mode for carrying out the invention. They are, obviously, not to be construed as limitative of the invention since various other embodiments can readily be evolved in view of the teachings provided herein.

EXAMPLE 1

ANTI-YEAST AND ANTI-FUNGAL ACTIVITY OF dl-CARVEOL

The anti-yeast and the anti-fungal compound contemplated by this invention is carveol which was studied for anti-yeast and anti-fungal activity against the organisms: *Candida albicans*, the yeast that causes infections of skin and mucus membranes; the cutaneous fungus *Microsporum canis*, that cause skin infections in man and animals; and the mildew causing fungi *Aureobasidium pullulans* OM 279C, *Cladosoorium cladosporiodes* OM 489, and *Phialophora liqnicola* OM 5922. The minimal effective concentration of carveol that kills yeast and the fungicidal concentration of carveol that kills fungi are listed in Tables B below. The carveol used in the tests was obtained from Aldrich Chemical Company, Milwaukee, Wis. The Catalogue Number and Lot Number for the carveol were 19,238-4 and 012487 BC respectively.

TABLE B
ANTI-YEAST AND ANTI-FUNGAL ACTIVITY OF dl CARVEOL

| ORGANISM | MINIMUM EFFECTIVE CONCENTRATION | | |
|---|---|---|---|
| A. YEAST | 10 MIN | 60 MIN | 24 HOURS |
| 1. *Candida albicans* | 0.06 | 0.02 | 0.005 |
| B. FUNGI | MINIMUM FUNGICIDAL CONCENTRATION | | |
| 1. *Microsoorum canis* | 0.01 | 0.01 | 0.01 |
| 2. *Aureobasidium pullulans* Om 279C | 0.02 | 0.02 | 0.01 |
| 3. *Cladosoorium cladosooriodes* OM 489 | 0.06 | 0.01 | 0.01 |
| 4. *Phialoohora lignicola* OM 5922 | 0.01 | 0.01 | 0.01 |

The standard assay used to test the activity of carveol against yeast and fungi was as follows: various dilutions of carveol were individually prepared in Sabouraud dextrose broth medium. An inoculum of $10^6$ colony-forming units (CFU/ml) of yeast or fungi were introduced into each test, after which it was incubated at 37° C. in air, and subcultured (0.01ml) at 10 minutes, 60 minutes, and 24 hours onto agar media free of carveol. Results were expressed as the minimal lethal concentration, i.e. the lowest concentration of carveol (ml carveol/total ml of test) with no detectable viable colonies following subculture onto media free of carveol.

Details of each assay are presented in Table C which follows.

TABLE C
Test conditions used to assay the anti-yeast and anti-fungal activity of carveol

| ORGANISM | BROTH MEDIUM | SUBCULTURE AGAR MEDIUM | INCUBATION CONDITIONS |
|---|---|---|---|
| 1. Yeast | Sabouraud dextrose | 5% sheep blood | air at 37° C. |
| 2. Fungi | Sabouraud dextrose | Sabouraud dextrose agar | air at 30° C. |

EXAMPLE 2

FORMULATIONS WHICH INCLUDE THE ANTI-YEAST AND ANTI-FUNGAL COMPOUND CARVEOL

The following formulations are prepared using carveol in solutions, gels, soaps, paints, pastes, creams, ointments, suppositories, tampons, aerosols, and emulsions. When yeast or fungi are treated with carveol containing formulations, the formulations kill or prevent the growth of yeast and fungi.

| CHEMICAL | % OF TOTAL | RANGE | ACTION |
|---|---|---|---|
| A. LIQUIDS | | | |
| 1. SOLUTIONS OR SPRAYS | | | |
| a. Carveol | 5.0% | 0.1-50% | fungicide |
| Corn Oil | 95.0% | 50-99.9% | diluent |
| | 100.0% | | |
| b. Carveol | 1.0% | 0.1-50% | fungicide |
| Ethyl Alcohol | 99.0% | 50-99.9% | diluent |
| | 100.0% | | |
| 2. MOUTHWASH | | | |
| a. Carveol | 50.0% | 0.1-50% | anti-yeast |
| Flavor | 2.0% | 1-5% | flavor |
| Ethyl Alcohol | 48.0% | 45-98.9% | diluent |
| | 100.0% | | |
| B. DENTIFRICE | | | |
| 1. LIQUID | | | |
| Liquid soap concentrate | 5.0% | 2-10% | surfactant |
| Saccharin | 0.2% | 0.1-1.0% | flavor |
| Clove Oil | 1.0% | 0.5-3.0% | flavor |
| Cinnamon Oil | 0.5% | 0.5-3.0% | flavor |
| Peppermint Oil | 0.5% | 0.5-3.0% | flavor |
| Ethyl Alcohol | 42.6% | 29.5-95.3% | diluent |
| Color | 0.2% | 0.1-0.5% | color |
| Carveol | 50.0% | 1-50% | fungicide |
| | 100.0% | | |
| 2. GEL | | | |
| Sodium monofluorophosphate | 0.8% | 0.5-1.5% | antiplaque |
| Carveol | 50.0% | 1-50% | anti-yeast |
| Hydrated silica xerogel | 10.0% | 8-15% | abrasive |
| Hydrated thickening silica | 8.5% | 5-10% | binder |
| Sorbitol 70% solution | 18.8% | 5-73.3% | humectant |
| Polyethylene glycol 32 | 5.0% | 3-7% | bodying agent |
| Sodium lauryl sulfate | 1.5% | 1-2% | surfactant |
| Carboxymethyl cellulose gum | 1.0% | 0.5-2% | binder |
| S D alcohol | 1.0% | 0.5-2% | stabilizer |
| Flavor | 3.0% | 2-4% | flavor |
| Saccharin | 0.2% | 0.1-0.5% | flavor |

-continued

| CHEMICAL | % OF TOTAL | RANGE | ACTION |
|---|---|---|---|
| F D & C Green #3 | 0.1% | 0.1-0.5% | color |
| F D & C Yellow #10 | 0.1% | 0.1-0.5% | color |
| | 100.0% | | |
| 3. PASTE | | | |
| Sodium monofluorophosphate | 0.8% | 0.5-1.5% | antiplaque |
| Carveol | 50.0% | 1-50% | fungicide |
| Dicalcium phosphate dihydrate | 22.0% | 20.4-30% | abrasive |
| Water | 16.0% | 11.1-69.5% | diluent |
| Glycerine | 5.1% | 4.5-12.5% | bodying agent |
| Flavor | 2.0% | 2-3% | flavor |
| Sodium lauryl sulfate | 1.5% | 1-2% | surfactant |
| Carboxymethyl cellulose gum | 1.4% | 0.5-2.0% | binder |
| Tetrasodium pyrophosphate | 1.0% | 0.5-2.0% | binder |
| Sodium saccharin | 0.2% | 0.1-0.5% | flavor |
| | 100.0% | | |

C. OINTMENTS & SUPPOSITORIES WITH AND WITHOUT HYDROCORTISONE

| CHEMICAL | % OF TOTAL | RANGE | ACTION |
|---|---|---|---|
| 1. OINTMENT WITH HYDROCORTISONE | | | |
| Carveol | 1.0% | 0.1-15.0% | fungicide |
| Polyethylene glycol 3350 | 59.5% | 48.5-59.7% | bodying agent & emulsifier |
| Polyethylene glycol 400 | 39.5% | 31.5-39.7% | bodying agent & emulsifier |
| Hydrocortisone | 1.0% | 0.5-5.0% | anti-inflammatory |
| | 100.0% | | |
| 2. OINTMENT WITHOUT HYDROCORTISONE | | | |
| Carveol | 1.0% | 0.1-15.0% | anti-yeast |
| Polyethylene glycol 3350 | 59.5% | 51.0-59.95% | bodying agent & emulsifier |
| Polyethylene glycol 400 | 39.5% | 34.0-39.95% | bodying agent & emulsifier |
| | 100.0% | | |
| 3. SUPPOSITORY WITHOUT HYDROCORTISONE | | | |
| Carveol | 1.0% | 0.1-15% | fungicide |
| Polyethylene glycol 1000 | 9.5% | 51.0-59.95% | bodying agent & emulsifier |
| Polyethylene glycol 3350 | 39.5% | 34.0-39.95% | bodying agent & emulsifier |
| | 100.0% | | |
| 4. SUPPOSITORY WITH HYDROCORTISONE | | | |
| Carveol | 1.0% | 0.1-15% | anti-yeast |
| Polyethylene glycol 1000 | 74.0% | 60.0-75.2% | bodying agent & emulsifier |
| Polyethylene glycol 3350 | 24.0% | 20.0-24.2% | bodying agent & emulsifier |
| Hydrocortisone | 1.0% | 0.5-5.0% | anti-inflammatory |
| | 100.0% | | |

D. CREAMS WITHOUT HYDROCORTISONE

| CHEMICAL | % OF TOTAL | RANGE | ACTION |
|---|---|---|---|
| 1. Carveol | 1.0% | 0.1-15.0% | fungicide |
| Cetyl alcohol | 15.0% | 12.0-18.0% | thickener |
| Arlacel 165** | 5.0% | 3.5-7.5% | emulsifier |
| Sorbitol 70% solution | 5.0% | 3.5-8.0% | humectant |
| Water | 74.5% | 51.5-80.9% | diluent |
| | 100.0% | | |
| 2. Carveol | 1.0% | 0.1-15.0% | anti-yeast |
| Spermaceti wax | 12.5% | 10.0-15.0% | thickener |
| Sorbitan monostearate | 10.0% | 7.5-12.5% | emulsifier |
| Polyethylene 20 Sorbitan monostearate | 6.0% | 4.0-8.0% | emulsifier |
| Water | 75.5% | 49.5-78.4% | diluent |
| | 100.0% | | |

E. CREAMS WITH HYDROCORTISONE

| CHEMICAL | % OF TOTAL | RANGE | ACTION |
|---|---|---|---|
| 1. Carveol | 1.0% | 0.1-15.0% | fungicide |

-continued

| CHEMICAL | % OF TOTAL | RANGE | ACTION |
|---|---|---|---|
| Cetyl alcohol | 15.0% | 12.0-18.0% | thickener |
| Arlacel 165** | 5.0% | 3.5-7.5% | emulsifier |
| Sorbitol 70% solution | 5.0% | 3.5-8.0% | humectant |
| Hydrocortisone | 1.0% | 0.5-5.0% | anti-inflammatory |
| Water | 73.0% | 46.5-80.4% | diluent |
| | 100.0% | | |

*Croda, Inc., 51 Madison Ave., New York, New York 10010
**Glycerol monostearate and polyoxyethylene stearate ICI of America (Formerly Atlas Chemical Industries), Wilmington, Delaware 19899

F. TAMPONS

| | % OF TOTAL | RANGE | ACTION |
|---|---|---|---|
| 1. Carveol 2 cc 2 Gm | 8% | 1-15% | anti-yeast |
| Tampon 23 Gm | 92% | 85-99% | reservoir for fungicide |
| | 100.0% | | |

G. AEROSOLS WITHOUT HYDROCORTISONE

| | % OF TOTAL | RANGE | ACTION |
|---|---|---|---|
| 1. Carveol | 5.0% | 0.5-50% | fungicide |
| Ethyl alcohol | 95.0% | 50-99.5% | diluent |
| | 100.0% | | |
| Pressurized nitrogen propellant at 100-125 psig | | | |
| 2. Carveol | 10.0% | 0.5-50.0% | fungicide |
| Soybean oil | 90.0% | 50.0-99.5% | diluent |
| | 100.0% | | |
| Pressurized nitrogen propellant at 100-125 psig | | | |

H. AEROSOL WITH HYDROCORTISONE

| | % OF TOTAL | RANGE | ACTION |
|---|---|---|---|
| 1. Carveol | 1.0% | 0.5-50% | anti-yeast |
| Soybean oil | 98.0% | 45-99.0% | diluent |
| Hydrocortisone | 1.0% | 0.5-5.0% | anti-inflammatory |
| | 100.0% | | |
| Pressurized nitrogen propellant at 100-125 psig | | | |

I. OIL IN WATER EMULSION

| | % OF TOTAL | RANGE | ACTION |
|---|---|---|---|
| 1. Carveol | 0.1% | 0.1-50% | fungicide |
| Corn oil | 10.0% | 10-15% | oil |
| Arlacel 40** | 2.0% | 1-3% | emulsifier |
| Tween 40 | 3.0% | 2-4% | emulsifier |
| 2. Water | 84.9% | 28-86.9% | diluent |
| | 100.0% | | |

Heat 1 to 70° C. Heat 2 to 72° C. Add 2 to 1 with agitation. Stir until cooled to room temperature.

J. OIL IN WATER EMULSION WITH SOAP (FUNGICIDAL SOAP)

| | % OF TOTAL | RANGE | ACTION |
|---|---|---|---|
| 1. Carveol | 1.0% | 0.1-25% | fungicide |
| Corn oil | 30.0% | 20.0-40.0% | oil |
| Arlacel 40** | 2.0% | 1.0-3.0% | emulsifier |
| Tween 40 | 3.0% | 2.0-4.0% | emulsifier |
| Liquid soap concentrate | 3.5% | 2.5-5.0% | surfactant |
| 2. Water | 60.5% | 23-74.4% | diluent |
| | 100.0% | | |

Heat 1 to 70° C. Heat 2 to 72° C. Add 2 to 1. Stir until cooled to room temperature.

K. WATER IN OIL EMULSION

| | % OF TOTAL | RANGE | ACTION |
|---|---|---|---|
| 1. Carveol | 1.0% | 0.1-25% | fungicide |
| Arlacel 186** | 3.0% | 2.0-4.0% | emulsifier |
| Soybean oil | 15.0% | 10.0-25.0% | oil |
| Ceresin wax | 0.5% | 0.3-0.6% | thickener |
| Beeswax | 0.5% | 0.3-0.6% | thickener |
| Tween 80 | 0.5% | 0.3-0.6% | emulsifier |
| 2. Water | 79.5% | 44.2-87.0% | diluent |
| | 100.0% | | |

Heat 1 to 70° C. Heat 2 to 72° C. Add 2 to 1 with continuous agitation.

L. PAINT

1. ENAMEL

| | % OF TOTAL | RANGE | ACTION |
|---|---|---|---|
| Carveol | 1.0% | 1-10% | fungicide |
| Titanium dioxide | 14.91% | 12-16% | pigment |
| Calcium carbonate | 29.83% | 25-35% | pigment |
| Silicate | 4.81% | 3-6% | pigment |
| Soya alkyd resin | 25.72% | 22-28% | pigment (binder) |
| Mineral spirits | 23.73% | 5-37% | solvent (thinner) |
| | 100.00% | | |

2. LATEX

| | % OF TOTAL | RANGE | ACTION |
|---|---|---|---|
| Carveol | 1.0% | 1-10% | fungicide |
| Titanium dioxide | 10.76% | 8-12% | pigment |
| Silicate | 12.91% | 10-16% | pigment |

-continued

| CHEMICAL | % OF TOTAL | RANGE | ACTION |
| --- | --- | --- | --- |
| Calcium carbonate | 20.91% | 15-25% | pigment |
| Vinyl acrylic resin solids | 12.22% | 10-16% | vehicle (binder) |
| Glycol | 8.47% | 6-10% | solvent (thinner) |
| Water | 34.0% | 12-50% | solvent (thinner) |
| | 100.0% | | |

While only certain preferred embodiments of this invention have been shown and described by way of illustration, many modifications will occur to those skilled in the art and it is, therefore, desired that it by understood that it is intended herein, to cover all such modifications that fall within the true spirit and scope of this invention.

We claim:

1. A method of killing fungi or yeast comprising treating fungi or yeast in their habitat with toxic concentrations of carveol.

2. The method of claim 1 for killing fungi wherein said fungi are selected from a group consisting of Microsporum, Aureobasidium, Cladosporium, and Phialophora.

3. A method of claim 1 for killing yeast wherein said yeast is Candida.